(12) United States Patent
Kane et al.

(10) Patent No.: US 9,962,550 B2
(45) Date of Patent: May 8, 2018

(54) SYSTEMS AND METHODS FOR RATE RESPONSIVE PACING WITH A LEADLESS CARDIAC PACEMAKER

(71) Applicant: CARDIAC PACEMAKERS, INC., St. Paul, MN (US)

(72) Inventors: Michael J. Kane, Roseville, MN (US); Jeffrey E. Stahmann, Ramsey, MN (US); Keith R. Maile, New Brighton, MN (US)

(73) Assignee: CARDIAC PACEMAKERS, INC., St. Paul, MN (US)

( * ) Notice: Subject to any disclaimer, the term of this patent is extended or adjusted under 35 U.S.C. 154(b) by 0 days. days.

(21) Appl. No.: 14/736,907

(22) Filed: Jun. 11, 2015

(65) Prior Publication Data
US 2015/0360036 A1     Dec. 17, 2015

Related U.S. Application Data

(60) Provisional application No. 62/011,249, filed on Jun. 12, 2014.

(51) Int. Cl.
*A61N 1/365*     (2006.01)
*A61N 1/368*     (2006.01)
(Continued)

(52) U.S. Cl.
CPC ..... *A61N 1/36585* (2013.01); *A61N 1/36542* (2013.01); *A61N 1/3756* (2013.01);
(Continued)

(58) Field of Classification Search
CPC .............. A61N 1/3756; A61N 1/36585; A61N 1/36542
See application file for complete search history.

(56) References Cited

U.S. PATENT DOCUMENTS 4,787,389 A  11/1988 Tarjan
5,197,467 A * 3/1993 Steinhaus .......... A61N 1/36521
                                              600/547
(Continued)

FOREIGN PATENT DOCUMENTS

EP          2471452 A1    7/2012
WO       2006065394 A1    6/2006

OTHER PUBLICATIONS

Notification of Transmittal of the International Search Report and the Written Opinion of the International Searching Authority, or the Declaration, dated Mar. 3, 2016, 11 pages.

*Primary Examiner* — William Levicky
(74) *Attorney, Agent, or Firm* — Seager, Tufte & Wickhem LLP

(57) ABSTRACT

Systems and methods for providing rate responsive pacing therapy to a heart of a patient. One example method for providing rate responsive pacing therapy includes sensing cardiac electrical data with a leadless cardiac pacemaker (LCP) that is implanted within or proximate the heart. From this location, the LCP may provide pacing therapy to the heart based at least in part on the sensed cardiac electrical data. An implantable medical device located remotely from the heart may sense patient activity, and may wirelessly communicate patient activity data from the implantable medical device to the LCP, sometimes using conducted communication. The LCP may be then determine an adjustment to the provided pacing therapy (e.g. adjust the pacing rate) based at least in part on the received patient activity data signal.

19 Claims, 8 Drawing Sheets

(51) Int. Cl.
  *A61N 1/375* (2006.01)
  *A61N 1/372* (2006.01)
  *A61N 1/05* (2006.01)

(52) U.S. Cl.
  CPC ........ *A61N 1/37288* (2013.01); *A61N 1/0563* (2013.01); *A61N 1/3684* (2013.01); *A61N 1/36521* (2013.01)

(56) References Cited

U.S. PATENT DOCUMENTS

| | | | |
|---|---|---|---|
| 5,411,535 A | 5/1995 | Fujii et al. | |
| 5,792,195 A * | 8/1998 | Carlson | A61N 1/36542 607/17 |
| 7,634,313 B1 * | 12/2009 | Kroll | A61N 1/37288 607/2 |
| 7,937,148 B2 | 5/2011 | Jacobson | |
| 8,315,701 B2 | 11/2012 | Cowan et al. | |
| 8,571,678 B2 | 10/2013 | Wang | |
| 8,744,572 B1 | 6/2014 | Greenhut et al. | |
| 2001/0051787 A1 * | 12/2001 | Haller | A61N 1/37211 604/66 |
| 2006/0129197 A1 * | 6/2006 | Zhang | A61N 1/3712 607/28 |
| 2006/0135999 A1 | 6/2006 | Bodner et al. | |
| 2007/0250123 A1 * | 10/2007 | Rutten | A61N 1/375 607/5 |
| 2011/0208260 A1 | 8/2011 | Jacobson | |
| 2012/0109236 A1 * | 5/2012 | Jacobson | A61N 1/368 607/4 |
| 2013/0041422 A1 | 2/2013 | Jacobson | |
| 2013/0282073 A1 | 10/2013 | Cowan et al. | |
| 2013/0325081 A1 | 12/2013 | Karst et al. | |
| 2014/0214104 A1 | 7/2014 | Greenhut et al. | |

* cited by examiner ity using multiple implanted devices within a patient. It is contemplated that the multiple implanted devices may include, for example, pacemakers, defibrillators, diagnostic devices, sensor devices, and/or any other suitable implantable devices, as desired. More specifically, the present disclosure relates to systems, devices, and methods for providing rate responsive pacing with a Leadless Cardiac Pacemaker (LCP).

SYSTEMS AND METHODS FOR RATE RESPONSIVE PACING WITH A LEADLESS CARDIAC PACEMAKER

CROSS-REFERENCES TO RELATED APPLICATIONS

This application claims the benefit of U.S. Provisional Application No. 62/011,249, filed Jun. 12, 2014, the complete disclosure of which is herein incorporated by reference.

TECHNICAL FIELD

The present disclosure generally relates to systems, devices, and methods for delivering pacing pulses to a heart and, more specifically to systems, devices, and methods for performing rate responsive pacing with a Leadless Cardiac Pacemaker (LCP).

BACKGROUND

Pacing instruments can be used to treat patients suffering from various heart conditions that may result in a reduced ability of the heart to deliver sufficient amounts of blood to a patient's body. These heart conditions may lead to rapid, irregular, and/or inefficient heart contractions. To help alleviate some of these conditions, various devices (e.g., pacemakers, defibrillators, etc.) can be implanted in a patient's body. Such devices may monitor and provide electrical stimulation to the heart to help the heart operate in a more normal, efficient and/or safe manner.

Pacing the heart at a fixed rate is limiting because it does not allow the heart rate to increase with increased metabolic demand. If the heart is paced at a constant rate, as for example by a VVI pacemaker, limitations are imposed upon the patient with respect to lifestyle and activities. It is to overcome these limitations and improve the quality of life of such patients that rate-responsive pacemakers have been developed.

Rate responsive capable pacemakers often include one or more sensors to gain insight into the current metabolic demand of the patient, and adjust the pacing rate accordingly. This can be accomplished relatively easily in a traditional pacemaker that has a pacemaker "can" implanted in a pocket under the skin, with leads extending into the heart. The pacemaker "can" is often sufficiently large to house a fairly high capacity battery and may have significant processing power. Also, the pacemaker may have access to signals and/or sensors that are located both inside the heart via the leads and outside of the heart via the "can".

Leadless Cardiac Pacemakers (LCP), which are implanted in or proximate to the heart, present a unique challenge to rate responsive pacing. For example, because of constant movement of the LCP with the heart, accelerometer data obtained from a local accelerometer within the LCP housing may have significant noise, which can require significant processing power to isolate movement that is due to the patient's activity versus movement cause by the beating of the heart itself. In another example, because of its location and size, it can be difficult for an LCP to derive a reliable measure of respiration rate and/or tidal volume of the patient, which can be an indicator of patient activity. These are just some of the challenges in providing effective rate responsive pacing in a LCP. What would be desirable are improved systems and methods for providing rate responsive pacing using a Leadless Cardiac Pacemaker (LCP).

SUMMARY

The present disclosure relates generally to systems and methods for coordinating treatment of abnormal heart activity using multiple implanted devices within a patient. It is contemplated that the multiple implanted devices may include, for example, pacemakers, defibrillators, diagnostic devices, sensor devices, and/or any other suitable implantable devices, as desired. More specifically, the present disclosure relates to systems, devices, and methods for providing rate responsive pacing with a Leadless Cardiac Pacemaker (LCP).

An illustrative method for providing rate responsive pacing therapy to a heart of a patient using a Leadless Cardiac Pacemaker (LCP) may include: sensing cardiac electrical data with an LCP implanted within or proximate the heart of the patient; providing pacing therapy to the heart of the patient with the LCP based at least in part on the sensed cardiac electrical data; sensing patient activity with an implanted medical device from a location that is spaced from the heart of the patient; wirelessly communicating a patient activity data signal from the implantable medical device to the LCP; and having the LCP determine an adjustment to the provided pacing therapy based at least in part on the received patient activity data signal, and adjusting the pacing therapy provided by the LCP. The adjustment may include an adjustment to the pacing rate so that the pacing rate changes with the activity level of the patient. In some cases, the patient activity data signal is based, at least in part, on an output of an accelerometer in the implantable medical device. It is also contemplated that respiration information, such as respiration rate and tidal volume, may be derived from the patient activity data signal (e.g. a change in amplitude of the patient activity data signal over time).

An illustrative implantable medical device system may include a leadless cardiac pacemaker (LCP) implantable within or proximate the heart of the patient. The LCP may be configured to sense cardiac electrical data and provide pacing therapy to the heart of the patient based at least in part on the sensed cardiac electrical data. The illustrative implantable medical device system may also include an implantable medical device implanted in a location that is spaced from the heart of the patient. The implantable medical device may be configured to sense patient activity and wirelessly communicate a patient activity data signal to the LCP. The LCP may then be configured to determine an adjustment to the provided pacing therapy based at least in part on the received patient activity data signal and adjust the pacing therapy. The adjustment may include an adjustment to the pacing rate so that the pacing rate changes with the activity level of the patient.

In another example, a method for providing rate responsive pacing therapy to a heart of a patient may include: sensing cardiac electrical data with a leadless cardiac pacemaker (LCP) implanted within or proximate the heart of the patient; providing pacing therapy to the heart of the patient with the LCP based at least in part on the sensed cardiac electrical data; sensing patient activity with an implanted medical device from a location that is spaced from the heart of the patient; wirelessly communicating a patient activity data signal from the implantable medical device to the LCP; and the LCP determining an adjustment to the provided pacing therapy based at least in part on the received patient activity data signal, and adjusting the pacing therapy provided with the LCP.

Alternatively or additionally to the example above, in another example, the patient activity data signal is based, at least in part, on an output of an accelerometer of the implantable medical device.

Alternatively or additionally to any of the examples above, in another example, the LCP may determine the adjustment to the provided pacing therapy based at least in part on both the output of the accelerometer of the implantable medical device and a respiration rate of the patient that is determined at least in part by the implantable medical device.

Alternatively or additionally to any of the examples above, in another example, the patient activity data signal comprises accelerometer data.

Alternatively or additionally to any of the examples above, in another example, the patient activity data signal is based, at least in part, on a respiration signal.

Alternatively or additionally to any of the examples above, in another example, the respiration signal is based, at least in part, on a measure related to an impedance across at least a portion of a lung of the patient.

Alternatively or additionally to any of the examples above, in another example, the respiration signal is based, at least in part, on an output of transthoracic impedance sensor of the implantable medical device.

Alternatively or additionally to any of the examples above, in another example, the method may further comprise determining a measure related to a respiratory rate of the patient based, at least in part, on a difference in an amplitude of the patient activity data signal communicated by the implantable medical device and an amplitude of the patient activity data signal that is received by the LCP.

Alternatively or additionally to any of the examples above, in another example, the method may further comprise determining a tidal volume parameter based, at least in part, on a difference in an amplitude of the patient activity data signal communicated by the implantable medical device and an amplitude of the patient activity data signal that is received by the LCP.

Alternatively or additionally to any of the examples above, in another example, the method may further comprise determining the measure related to the impedance across at least a portion of a lung of the patent by: delivering a voltage pulse with the implantable medical device; measuring an amplitude of a delivered current of the delivered voltage pulse with the implantable medical device; communicating the measured amplitude of the delivered current from the implantable medical device to the LCP; measuring an amplitude of the delivered voltage pulse with the LCP; determining at the LCP the measure related to the impedance across the lungs of the patient based, at least in part, on the measured amplitude of the delivered voltage pulse and the measured amplitude of the delivered current communicated by the implantable medical device to the LCP.

Alternatively or additionally to any of the examples above, in another example, the method may further comprise determining a tidal volume parameter based on a difference in an amplitude of the patient activity data signal communicated from the implantable medical device and an amplitude of the patient activity data signal received by the LCP; determining a minute ventilation parameter based on a determined respiratory rate and the determined tidal volume parameter; and the LCP determining the adjustment to the provided pacing therapy based at least in part on both the received patient activity data signal and the determined minute ventilation.

Alternatively or additionally to any of the examples above, in another example, the patient activity data signal may comprise one or more of an electrical signal, a radiofrequency signal and an acoustic signal.

Alternatively or additionally to any of the examples above, in another example, the patient activity data signal is based, at least in part, on a sensed heart rate of the patient.

In another example, a method for providing rate responsive pacing therapy to a heart of a patient comprises: sensing cardiac electrical data with a leadless cardiac pacemaker (LCP) implanted within or proximate the heart of the patient; providing pacing therapy to the heart of the patient with the LCP based at least in part on the sensed cardiac electrical data; wirelessly communicating signals from the LCP to an implantable medical device implanted remote from the heart of the patient; and with the implantable medical device, determining one or more physiological parameters based at least in part on the wirelessly communicated signals.

Alternatively or additionally to the example above, in another example, the method may further comprise sensing patient activity with the implantable medical device.

Alternatively or additionally to any of the examples above, in another example, the method may further comprise communicating a patient activity data signal from the implantable medical device to the LCP; and with the LCP, adjusting the provided pacing therapy based at least in part on the received patient activity data signal.

Alternatively or additionally to any of the examples above, in another example, the method may further comprise with the implantable medical device, determining a measure related to a transthoracic impedance based on the received wireless communication signals from the LCP.

Alternatively or additionally to any of the examples above, in another example, determining the measure related to the transthoracic impedance based on the received wireless communication signals from the LCP may comprise: delivering a voltage pulse with the LCP; measuring an amplitude of a delivered current from the delivered voltage pulse with the LCP, wherein the received wireless communication signals comprise the measured amplitude of the delivered current; measuring an amplitude of the delivered voltage pulse with the implantable medical device; and determining a measure related to the transthoracic impedance with the implantable medical device based on the measured amplitude of the delivered voltage pulse and the received measured amplitude of the delivered current.

Alternatively or additionally to any of the examples above, in another example, the one or more physiological parameters may comprise one or more of respiratory rate, tidal volume and heart rate.

Alternatively or additionally to any of the examples above, in another example, determining one or more physiological parameters based on the wirelessly communicated signals may comprise determining a difference in an amplitude of the wirelessly communicated signals delivered by the LCP and an amplitude of the wirelessly communicated signals sensed by the implantable medical device.

Alternatively or additionally to any of the examples above, in another example, the wirelessly communicated signals comprise pacing pulses.

Alternatively or additionally to any of the examples above, in another example, the wirelessly communicated signals comprise sub-threshold electrical pulses.

Alternatively or additionally to any of the examples above, in another example, the wirelessly communicated signals comprise pacing pulses if a rate of delivered pacing pulses by the LCP exceeds a predetermined threshold, and wherein the wirelessly communicated signals comprise sub-threshold electrical pulses if the rate of delivered pacing pulses by the LCP is equal to or less than a predetermined threshold.

Alternatively or additionally to any of the examples above, in another example, the method may further comprise communicating one or more of the one or more determined physiological parameters from the implantable medical device to the LCP; and with the LCP, adjusting the provided pacing therapy based at least in part on the received determined physiological parameters.

Alternatively or additionally to any of the examples above, in another example, the method further comprising sensing a patient activity level using the implantable medical device; and communicating one or more parameters from the implantable medical device to the LCP, the one or more parameters based at least in part on the one or more determined physiological parameters and the patient activity level; and with the LCP, adjusting the provided pacing therapy based at least in part on the received one or more parameters.

Alternatively or additionally to any of the examples above, in another example, the one or more parameters includes a rate responsive heart rate.

In another example, an implantable medical device system for providing adjustable rate pacing therapy to a heart of a patient comprises: a leadless cardiac pacemaker (LCP) implantable within or proximate the heart of the patient; and an implantable medical device, wherein the implantable medical device: comprises an accelerometer; implantable remote from the heart of the patient; and is wirelessly communicatively coupled to the LCP; wherein the implantable medical device is configured to generate patient activity data based at least in part on an output of the accelerometer, and is further configured to wirelessly communicate the patient activity data to the LCP; and wherein the LCP is configured to: provide rate responsive pacing therapy to the heart of the patient; and adjust the rate of the rate responsive pacing therapy based at least in part on the patient activity data received from the implantable medical device.

Alternatively or additionally to any of the examples above, in another example, the implantable medical device is further configured to: determine when a rate of change in a vertical component of a three-axis accelerometer rises above a predetermined threshold; and communicate the patient activity data to the LCP when the rate of change in the vertical component of the three-axis accelerometer rises above a predetermined threshold.

Alternatively or additionally to any of the examples above, in another example, the patient activity data comprises a heart rate.

Alternatively or additionally to any of the examples above, in another example, the patient activity data comprises data from a three-axis accelerometer, and wherein the LCP is further configured to: determine when a rate of change in a vertical component of the three-axis accelerometer rises above a predetermined threshold; and adjust the rate of the rate-adjustable pacing therapy based on the patient activity data received from the implantable medical device.

In another example, an implantable medical device system for providing adjustable rate pacing therapy to a heart of a patient comprises: a leadless cardiac pacemaker (LCP) implantable within or proximate the heart of the patient, wherein the LCP is configured to: sense cardiac electrical data, and provide pacing therapy to the heart of the patient based at least in part on the sensed cardiac electrical data; and an implantable medical device implanted in a location that is spaced from the heart of the patient, wherein the implantable medical device is configured to: sense patient activity, and wirelessly communicate a patient activity data signal to the LCP; and wherein the LCP is configured to determine an adjustment to the provided pacing therapy based at least in part on the received patient activity data signal and adjusts the pacing therapy.

Alternatively or additionally to any of the examples above, in another example, the patient activity data signal is based, at least in part, on an output of an accelerometer of the implantable medical device.

Alternatively or additionally to any of the examples above, in another example, the LCP is further configured to determine the adjustment to the provided pacing therapy based at least in part on both the output of the accelerometer of the implantable medical device and a respiration rate of the patient that is determined at least in part by the implantable medical device.

Alternatively or additionally to any of the examples above, in another example, the patient activity data signal comprises accelerometer data.

Alternatively or additionally to any of the examples above, in another example, the patient activity data signal is based, at least in part, on a respiration signal.

Alternatively or additionally to any of the examples above, in another example, the respiration signal is based, at least in part, on a measure related to an impedance across at least a portion of a lung of the patient.

Alternatively or additionally to any of the examples above, in another example, the respiration signal is based, at least in part, on an output of transthoracic impedance sensor of the implantable medical device.

Alternatively or additionally to any of the examples above, in another example, the LCP is further configured to determine a measure related to a respiratory rate of the patient based, at least in part, on a difference in an amplitude of the patient activity data signal communicated by the implantable medical device and an amplitude of the patient activity data signal that is received by the LCP.

Alternatively or additionally to any of the examples above, in another example, the LCP is further configured to determine a tidal volume parameter based, at least in part, on a difference in an amplitude of the patient activity data signal communicated by the implantable medical device and an amplitude of the patient activity data signal that is received by the LCP.

Alternatively or additionally to any of the examples above, in another example, the LCP is further configured to determine the measure related to the impedance across at least a portion of a lung of the patent by: receiving a measured amplitude of a delivered current from the implantable medical device after the implantable medical device delivers a voltage pulse and measures the amplitude of the delivered current of the delivered voltage pulse; measuring an amplitude of the delivered voltage pulse; and determining the measure related to the impedance across the lungs of the patient based, at least in part, on the measured amplitude of the delivered voltage pulse and the measured amplitude of the delivered current communicated by the implantable medical.

Alternatively or additionally to any of the examples above, in another example, the LCP is further configured to:

determine a tidal volume parameter based on a difference in an amplitude of the patient activity data signal communicated from the implantable medical device and an amplitude of the patient activity data signal received by the LCP; determine a minute ventilation parameter based on a determined respiratory rate and the determined tidal volume parameter; and determine the adjustment to the provided pacing therapy based at least in part on both the received patient activity data signal and the determined minute ventilation.

Alternatively or additionally to any of the examples above, in another example, the patient activity data signal comprises one or more of an electrical signal, a radiofrequency signal and an acoustic signal.

Alternatively or additionally to any of the examples above, in another example, the patient activity data signal is based, at least in part, on a sensed heart rate of the patient.

Alternatively or additionally to any of the examples above, in another example, the implantable medical device is further configured to: determine when a rate of change in a vertical component of a three-axis accelerometer rises above a predetermined threshold connected to the implantable medical device; and communicate the patient activity data to the LCP when the rate of change in the vertical component of the three-axis accelerometer rises above a predetermined threshold.

Alternatively or additionally to any of the examples above, in another example, the patient activity data signal includes three-axis accelerometer data, and the LCP is further configured to: determine when a rate of change in a vertical component of the three-axis accelerometer data rises above a predetermined threshold; and adjust the rate of the rate-adjustable pacing therapy when the rate of change in the vertical component of the three-axis accelerometer data rises above a predetermined threshold.

The above summary is not intended to describe each example embodiment or every implementation of the present disclosure. Advantages and attainments, together with a more complete understanding of the disclosure, will become apparent and appreciated by referring to the following description and claims taken in conjunction with the accompanying drawings.

BRIEF DESCRIPTION OF THE DRAWINGS

The disclosure may be more completely understood in consideration of the following description of various illustrative embodiments in connection with the accompanying drawings, in which.

Figure 1:
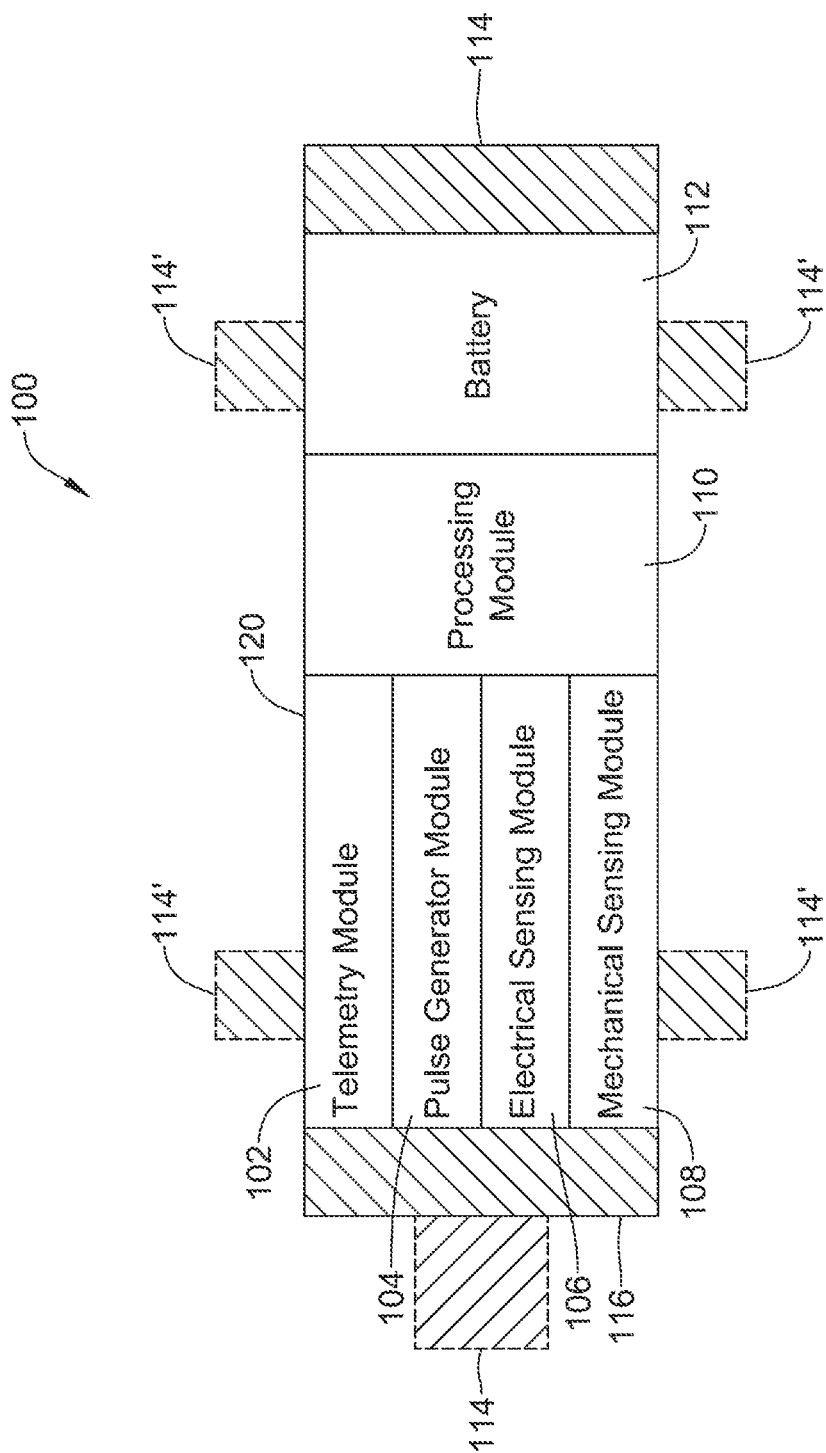
FIG. 1 illustrates an exemplary leadless cardiac pacemaker (LCP) having electrodes, according to one example of the present disclosure.

While the disclosure is amenable to various modifications and alternative forms, specifics thereof have been shown by way of example in the drawings and will be described in detail. It should be understood, however, that the intention is not to limit aspects of the disclosure to the particular illustrative embodiments described. On the contrary, the intention is to cover all modifications, equivalents, and alternatives falling within the spirit and scope of the disclosure.

DESCRIPTION

The following description should be read with reference to the drawings in which similar elements in different drawings are numbered the same. The description and the drawings, which are not necessarily to scale, depict illustrative embodiments and are not intended to limit the scope of the disclosure.

A normal, healthy heart induces contraction by conducting intrinsically generated electrical signals throughout the heart. These intrinsic signals cause the muscle cells or tissue of the heart to contract. This contraction forces blood out of and into the heart, providing circulation of the blood throughout the rest of the body. However, many patients suffer from cardiac conditions that affect this contractility of their hearts. For example, some hearts may develop diseased tissues that no longer generate or conduct intrinsic electrical signals. Such patients may need a medical device to deliver pacing pulses to their heart in order to cause their heart to contract and pump blood.

Figure 2:
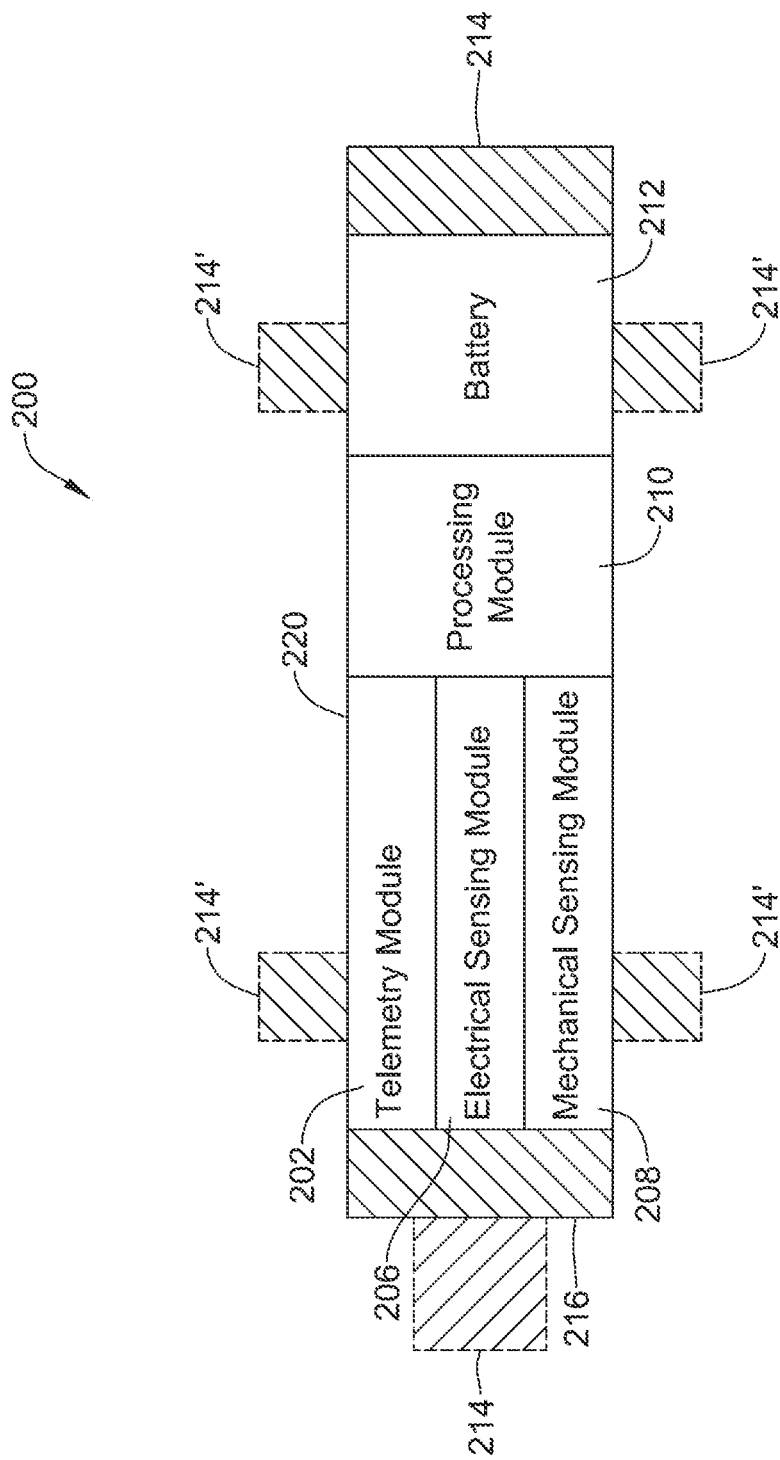
FIG. 2 illustrates a block diagram of an exemplary medical device that may be used in accordance with various examples of the present disclosure.
Figure 3:
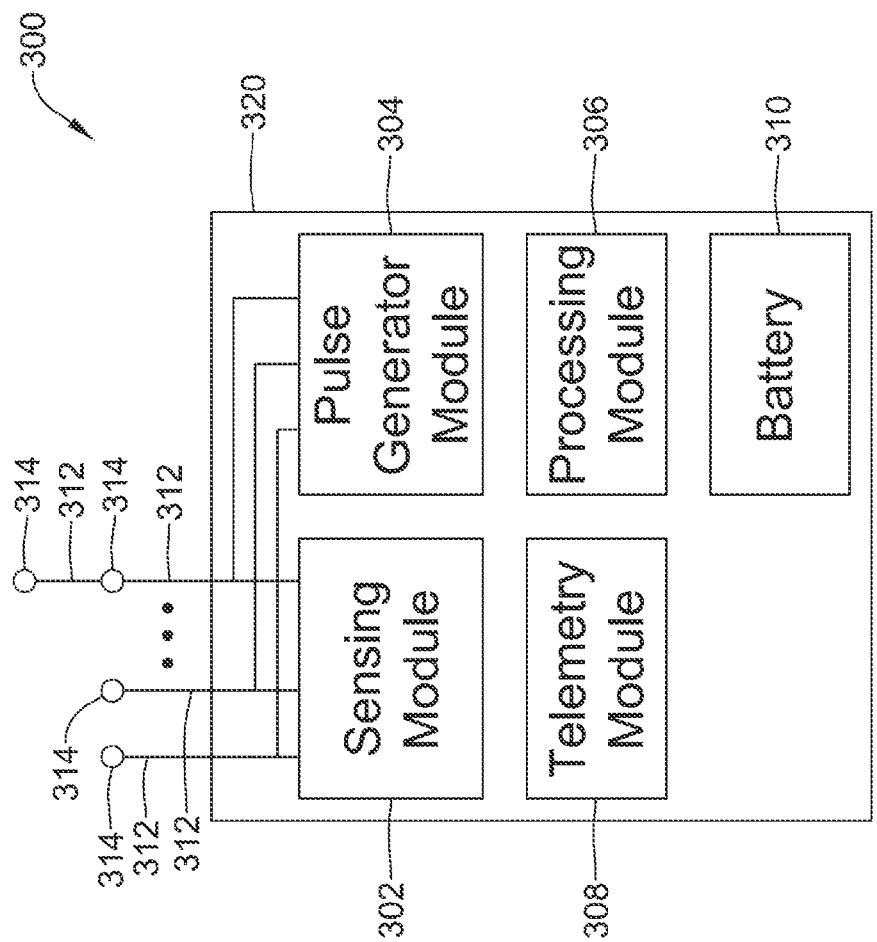
FIG. 3 illustrates a block diagram of another exemplary medical device that may be used in accordance with various examples of the present disclosure.

FIGS. 1-3 generally depict implantable medical devices that may be used for delivering pacing therapy to a heart of a patient. More specifically, the devices depicts in FIGS. 1-3 may be used alone or in various combinations to deliver rate responsive pacing therapy to a heart of a patient. Rate responsive pacing therapy may include pacing therapy where the rate of delivered pacing pulses change over time. In some cases, the pacing rate may be based on the current cardiovascular need of the patient, such as the activity level of the patient.

FIG. 1 depicts an exemplary leadless cardiac pacemaker (LCP) that may be implanted into a patient and may operate to deliver one or more types of pacing therapy to the heart. In some examples, the LCP may deliver pacing pulses in accordance with one or more therapies, such as rate responsive pacing therapy, anti-tachycardia pacing (ATP) therapy, cardiac resynchronization therapy (CRT), bradycardia therapy, defibrillation therapy, and/or the like. As can be seen in FIG. 1, LCP 100 may be a compact device with all components housed within or on housing 120. In the example shown in FIG. 1, LCP 100 may include telemetry module 102, pulse generator module 104, electrical sensing module 106, mechanical sensing module 108, processing module 110, battery 112, and electrodes 114.

Telemetry module 102 may be configured to communicate with devices such as sensors, other medical devices, and/or the like, that are located externally to LCP 100. Such devices may be located either external or internal to the patient's body. Irrespective of their location, external devices (i.e. external to the LCP 100 but not necessarily external to the patient's body) can communicate with LCP 100 via telemetry module 102 to accomplish one or more desired functions. For example, LCP 100 may communicate sensed electrical signals to an external medical device through telemetry module 102. In some cases, the external medical device may use the communicated electrical signals to determine occurrences of arrhythmias, deliver electrical stimulation therapy, and/or perform other functions.

In the example shown, LCP 100 may receive sensed electrical signals from an external medical device through telemetry module 102. In some cases, the LCP 100 may use the received sensed electrical signals to determine occurrences of arrhythmias, deliver electrical stimulation therapy, and/or perform other functions. In some cases, telemetry module 102 may be configured to use one or more methods for communicating with external devices. For example, telemetry module 102 may communicate via radiofrequency (RF) signals, inductive coupling, optical signals, acoustic signals, conducted communication signals, and/or any other signals suitable for communication. Communication techniques between LCP 100 and external devices will be discussed in further detail with reference to FIG. 4 below.

Pulse generator module 104 of LCP 100 may be electrically connected to electrodes 114. In some examples, LCP 100 may additionally include electrodes 114'. In such examples, pulse generator 104 may additionally be electrically connected to electrodes 114', but this is not required. Pulse generator module 104 may be configured to generate electrical stimulation signals, such as pacing pulses. For example, pulse generator module 104 may generate electrical stimulation signals by using energy stored in battery 112 within LCP 100, and deliver the generated electrical stimulation signals via electrodes 114 and/or 114'. In some examples, pulse generator module 104 or LCP 100 may include switching circuitry to selectively connect one or more of electrodes 114 and/or 114' to pulse generator module 104 in order to select via which electrodes 114/114' pulse generator 104 delivers the electrical stimulation therapy. Pulse generator module 104 may generate electrical stimulation signals with particular features or in particular sequences in order to provide one or multiple of a number of different stimulation therapies. For example, pulse generator module 104 may be configured to generate electrical stimulation signals to provide electrical stimulation therapy to combat bradycardia arrhythmias, tachyarrhythmia arrhythmias, fibrillation arrhythmias, and/or cardiac synchronization arrhythmias. In other examples, pulse generator module 104 may be configured to generate electrical stimulation signals to provide electrical stimulation therapies different than those described herein to treat one or more cardiac conditions.

In some examples, LCP 100 may include electrical sensing module 106 and/or mechanical sensing module 108. Electrical Sensing module 106 may be configured to sense electrical cardiac activity of the heart. In some cases, electrical sensing module 106 may be connected to electrodes 114/114', and electrical sensing module 106 may receive cardiac electrical signals conducted through electrodes 114/114'. In some instances, the cardiac electrical signals may represent local information from the chamber in which LCP 100 is implanted. For instance, if LCP 100 is implanted within a ventricle of the heart, cardiac electrical signals sensed by LCP 100 through electrodes 114/114' may represent ventricular cardiac electrical signals. In some cases, the cardiac electrical signals may represent remote information that emanates from outside of the chamber in which LCP 100 is implanted. These can be considered far-field signals.

Mechanical sensing module 108 may include, or be electrically connected to, various sensors, such as accelerometers, blood pressure sensors, heart sound sensors, blood-oxygen sensors, and/or other sensors that measure one or more physiological parameters of the heart and/or patient. Both electrical sensing module 106 and mechanical sensing module 108 may be connected to processing module 110, and may provide signals representative of the sensed electrical activity or physiological parameters to processing module 110. Although described with respect to FIG. 1 as separate sensing modules, in some examples, electrical sensing module 206 and mechanical sensing module 208 may be combined into a single module if desired.

Processing module 110 can be configured to control the operation of LCP 100. For example, processing module 110 may be configured to receive electrical signals from electrical sensing module 106. Based on the received signals, processing module 110 may determine occurrences and types of arrhythmias and/or other conditions. Based on any determined arrhythmias and/or other conditions, processing module 110 may control pulse generator module 104 to generate electrical stimulation in accordance with one or more therapies to treat the determined arrhythmias and/or other conditions. In some cases, processing module 110 may receive information from telemetry module 102, and may use such received information in determining whether an arrhythmia and/or other condition is occurring, determine a type of arrhythmia and/or other condition, and/or to take particular action in response to the received information. Processing module 110 may additionally control telemetry module 108 to send information to other devices.

In some examples, processing module 110 may include a pre-programmed chip, such as a very-large-scale integration (VLSI) chip or an application specific integrated circuit (ASIC). In such instances, the chip may be pre-programmed with control logic in order to control the operation of LCP 100. By using a pre-programmed chip, processing module 110 may use less power than other programmable circuits while still maintaining desired functionality, which may increase the battery life of LCP 100. In some cases, processing module 110 may include a programmable microprocessor. Such a programmable microprocessor may allow a user to adjust the control logic of LCP 100 after the LCP is manufactured, thereby allowing greater programming flexibility of LCP 100 over a pre-programmed chip. However, such programmable microprocessor may be less energy efficient than a pre-programmed chip.

In some examples, processing module 110 may include a memory circuit, and processing module 110 may store information on and/or read information from the memory circuit. In some instances, LCP 100 may include a separate memory circuit (not shown) that is in communication with processing module 110, such that processing module 110 may read and/or write information to and/or from the separate memory circuit.

Battery 112 may provide a power source to LCP 100 for its operations. In some examples, battery 112 may be a non-rechargeable lithium-based battery, or other non-rechargeable battery. Because LCP 100 is an implantable device, access to LCP 100 may be limited. Accordingly, it is desirable to have sufficient battery capacity to deliver therapy over a period of treatment such as days, weeks, months, or years. In some instances, battery 112 may a rechargeable lithium-based battery, or other rechargeable battery, in order to facilitate increasing the useable lifespan of LCP 100.

As depicted in FIG. 1, LCP 100 may include electrodes 114, which can be secured relative to housing 120 but exposed to the tissue and/or blood surrounding LCP 100. In some cases, electrodes 114 may be generally disposed on either end of LCP 100 and may be in electrical communication with one or more of modules 102, 104, 106, 108, and 110. Electrodes 114 may be supported by the housing 120. In some examples, electrodes 114 may be connected to housing 120 only through short connecting wires such that electrodes 114 are not directly secured relative to housing 120.

In some examples, LCP 100 may additionally include one or more electrodes 114'. Electrodes 114' may be positioned on the sides of LCP 100 and may increase the number of electrodes by which LCP 100 may sense cardiac electrical activity, deliver electrical stimulation and/or communicate with an external medical device. Electrodes 114 and/or 114' can be made up of one or more biocompatible conductive materials such as various metals or alloys that are known to be safe for implantation within a human body. In some instances, electrodes 114 and/or 114' connected to LCP 100 may have an insulative portion that electrically isolates the electrodes 114 from adjacent electrodes, housing 120, and/or other materials.

To implant LCP 100 inside a patient's body, an operator (e.g., a physician, clinician, etc.), may fix LCP 100 to the cardiac tissue of the patient's heart. To facilitate fixation, LCP 100 may include one or more anchors 116. Anchor 116 may include any one of a number of fixation or anchoring mechanisms. For example, anchor 116 may include one or more pins, staples, threads, screws, helix, tines, and/or the like. In some examples, although not shown, anchor 116 may include threads on its external surface that may run along at least a partial length of anchor 116. The threads may provide friction between the cardiac tissue and the anchor to help fix the anchor 116 within the cardiac tissue. In other examples, anchor 116 may include other structures such as barbs, spikes, or the like to facilitate engagement with the surrounding cardiac tissue.

FIG. 2 illustrates a block diagram of an exemplary medical device, MD 200, that may be used in accordance with various examples of the present disclosure. In some cases, MD 200 may be implanted into a patient, and may operate to sense one or more signals representative of a physiological condition of the patient. In some cases, MD 200 may be implanted in a location that is spaced from the heart of the patient. A device such as depicted in FIG. 2 may be used in conjunction with a device similar to that depicted in FIG. 1 to deliver rate responsive pacing to a heart of a patient. As can be seen in FIG. 2, MD 200 may be a compact device with all components housed within MD 200 or directly on housing 220. As illustrated in FIG. 2, MD 200 may include telemetry module 202, electrical sensing module 206, mechanical sensing module 208, processing module 210, battery 212, and electrodes 214/214'.

In some examples, MD 200 may be similar to LCP 100 as described with respect to FIG. 1. For example, telemetry module 202, electrical sensing module 206, mechanical sensing module 208, processing module 210, battery 212, and electrodes 214/214' may be similar to telemetry module 102, electrical sensing module 106, mechanical sensing module 108, processing module 110, battery 112, and electrodes 114/114', as described with respect to FIG. 1. In some cases, MD 200 may not include a pulse generator module. Accordingly, in some examples, MD 200 may be the same as LCP 100 with some hardware differences. Alternatively, MD 200 may include all of the components of LCP 100 (and in some cases, a duplicate device), except that one or more of the components may be disabled and/or not used, such as a pulse generator module. In some cases, using the same hardware may reduce the cost of the overall system by reducing the number of SKU's that need to be developed, tested, and then maintained and inventoried.

In some instances, MD 200 may include substantially different hardware than LCP 100. For example, MD 200 may be substantially different in size, shape and/or configuration from LCP 100. For instance, MD 200 may not require as severe of size constrained as LCP 100 due to typical implant locations for MD 200. In such examples, MD 200 may include, for example, a larger battery and/or more powerful processing unit than LCP 100.

FIG. 3 illustrates a block diagram of another exemplary medical device that may be used in accordance with various examples of the present disclosure. FIG. 3 depicts a medical device (MD) 300, which may be used in conjunction with a device similar to LCP 100 in order to help deliver rate responsive pacing. In the example shown, MD 300 may include telemetry module 308, pulse generator module 304, sensing module 302, processing module 306 and battery 310. Each of these modules may be similar to modules 102, 104, 106/108, 110 and 112 of LCP 100. In some examples, MD 300 may include a larger volume within housing 320 than LCP 100. In such examples, MD 300 may include a larger battery 310 and/or a processing module 306 capable of handling more complex operations than processing module 110 of LCP 100.

While MD 300 may be another leadless device such as shown in FIG. 1, in some instances MD 300 may includes leads such as leads 312. Leads 312 may include electrical wires that conduct electrical signals between electrodes 314 and one or more modules located within housing 320. Leads 312 may be connected to and extend away from housing 320 of MD 300. In some examples, leads 312 are implanted on or within a heart of a patient. Leads 312 may contain one or more electrodes 314 positioned at various locations on leads 312 and distances from housing 320. Some leads 312 may only include a single electrode 314 while other leads 312 may include multiple electrodes 314. Generally, electrodes 314 are positioned on leads 312 such that when leads 312 are implanted within the patient, one or more of the electrodes 314 are positioned to perform a desired function. In some cases, the one or more of the electrodes 314 may be in contact with the patient's cardiac tissue. In some cases, electrodes 314 may conduct intrinsically generated electrical signals to leads 312, e.g. signals representative of intrinsic cardiac electrical activity. Leads 312 may, in turn, conduct the received electrical signals to one or more of the modules 302, 304, 306, and 308 of MD 300. In some cases, MD 300 may generate electrical stimulation signals, and leads 312 may conduct the generated electrical stimulation signals to electrodes 314. Electrodes 314 may conduct the electrical signals to the cardiac tissue of the patient.

While not required, in some examples MD 300 may be an implantable medical device. In such examples, housing 320 of MD 300 may be implanted in a transthoracic region of the patient. Housing 320 may generally include any of a number of known materials that are safe for implantation in a human body and may, when implanted, hermetically seal the various components of MD 300 from fluids and tissues of the patient's body.

In some cases, MD 300 may be an implantable cardiac pacemaker (ICP). In this example, MD 300 may have one or more leads, for example leads 312, which are implanted on or within the patient's heart. The one or more leads 312 may include one or more electrodes 314 that are in contact with cardiac tissue and/or blood of the patient's heart. MD 300 may be configured to sense intrinsically generated cardiac electrical signals and determine, for example, one or more cardiac arrhythmias based on analysis of the sensed signals. MD 300 may be configured to deliver CRT, ATP therapy, bradycardia therapy, and/or other therapy types via leads 312 implanted within the heart. In some examples, MD 300 may additionally be configured provide defibrillation therapy.

In some instances, MD 300 may be an implantable cardioverter-defibrillator (ICD). In such examples, MD 300 may include one or more leads implanted within a patient's heart. MD 300 may also be configured to sense cardiac electrical signals, determine occurrences of tachyarrhythmias based on the sensed signals, and may be configured to deliver defibrillation therapy in response to determining an occurrence of a tachyarrhythmia. In other examples, MD 300 may be a subcutaneous implantable cardioverter-defibrillator (S-ICD). In examples where MD 300 is an S-ICD, one of leads 312 may be a subcutaneously implanted lead. In at least some examples where MD 300 is an S-ICD, MD 300 may include only a single lead which is implanted subcutaneously, but this is not required. In other cases, MD 300 may be a transvenous pacemaker and/or transveneous ICD.

In some examples, MD 300 may not be an implantable medical device. Rather, MD 300 may be a device external to the patient's body, and may include skin-electrodes that are placed on a patient's body. In such examples, MD 300 may be able to sense surface electrical signals (e.g. cardiac electrical signals that are generated by the heart or electrical signals generated by a device implanted within a patient's body and conducted through the body to the skin) In such examples, MD 300 may be configured to deliver various types of electrical stimulation therapy, including for example defibrillation therapy.

In some cases, leads 312 may contain one or more sensors, such as accelerometers, blood pressure sensors, heart sound sensors, blood-oxygen sensors, and/or other sensors which are configured to measure one or more physiological parameters of the heart and/or patient. In such examples, electrical and/or mechanical sensing module(s) 306, 308 may be in electrical communication with leads 312 and may receive signals generated from such sensors.

Figure 4:
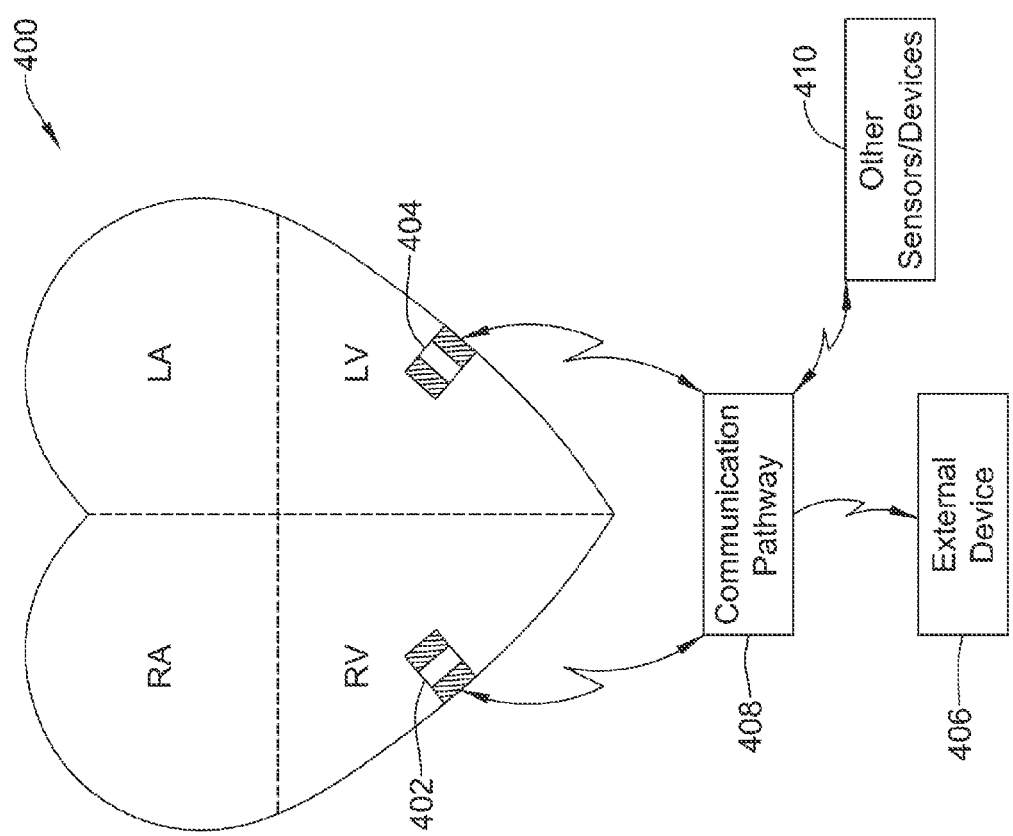
FIG. 4 is a schematic diagram of an exemplary medical system that includes multiple leadless cardiac pacemakers (LCPs) and/or other devices in communication with one another.

FIG. 4 illustrates an example of a medical device system and a communication pathway via which multiple medical devices may communicate. In the example shown, medical device system 400 may include LCPs 402 and 404, external medical device 406, and other sensors/devices 410. External device 406 may be any of the devices described previously with respect to FIGS. 2 and 3. Other sensors/devices 410 may also be any of the devices described previously with respect to 2 and 3. In other examples, other sensors/devices 410 may include a sensor, such as an accelerometer, respiration sensor or blood pressure sensor, or the like. In still other examples, other sensors/devices 410 may include an external programmer device that may be used to program one or more devices of system 400.

Various devices of system 400 may communicate via communication pathway 408. For example, LCPs 402, 404, external device 406 may sense intrinsic cardiac electrical signals and may communicate such signals to one or more other devices 402/404, 406, and 410 of system 400 via communication pathway 408. In one example, one or more of devices 402/404 may receive such signals and, based on the received signals, determine an occurrence of an arrhythmia or other heart function abnormality. In some cases, device or devices 402/404 may communicate such determinations to one or more other devices 406 and 410 of system 400. Additionally, one or more of devices 402/404, 406, and 410 of system 400 may take action based on the communicated determinations, such as by delivering appropriate electrical stimulation. This description is just one of many reasons for communication between the various devices of system 400. It is contemplated that communication pathway 408 may communicate using RF signals, inductive coupling, optical signals, acoustic signals, or any other signals suitable for communication.

In some cases, communication pathway 408 communicates using conducted communication. Accordingly, devices of system 400 may have components that allow for conducted communication. For instance, the devices of system 400 may send conducted communication signals (e.g. pulses) into the patient's body via one or more electrodes of a transmitting device, and may receive the conducted communication signals (e.g. pulses) via one or more electrodes of a receiving device. The patient's body may conduct the conducted communication signals (e.g. pulses) from the one or more electrodes of the transmitting device to the one or more electrodes of the receiving device in the system 400. In such examples, the delivered conducted communication signals (e.g. pulses) may differ from pacing or other therapy signals. For example, the devices of system 400 may deliver electrical communication pulses at an amplitude/pulse width that is sub-threshold to the heart. In some cases, the amplitude/pulse width of the delivered electrical communication pulses may be above the capture threshold of the heart, but may be delivered during a refractory period of the heart and/or may be incorporated in or modulated onto a pacing pulse, if desired.

In some cases, delivered electrical communication pulses may be modulated in any suitable manner to encode communicated information. In some cases, the communication pulses may be pulse width modulated. Alternatively, or in addition, the time between pulses may be modulated to encode desired communicated information. In some cases, conducted communication pulses may be voltage pulses, current pulses, biphasic voltage pulses, biphasic current pulses, or any other suitable electrical pulse as desired.

Figure 5:
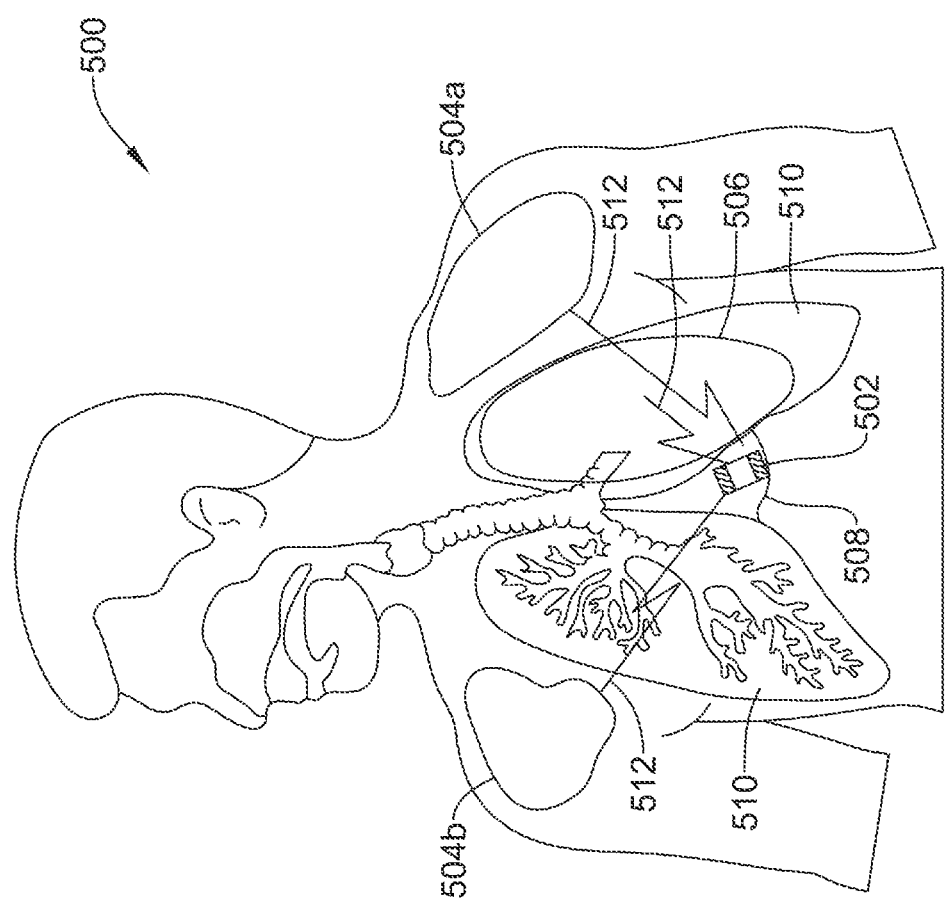
FIG. 5 is a diagram of an internal area of a chest cavity of a patient showing multiple illustrative regions where one or more devices may be implanted to help coordinate delivery of rate responsive pacing using an LCP, in accordance with one example of the present disclosure.

FIG. 5 illustrates example locations of implantation for one or more medical devices of a medical device system, such as those described with respect to FIGS. 1-3. FIG. 5 depicts an LCP 502, which may be similar to LCP 100, implanted within heart 508 of patient 500. Regions 504A-B depict example regions where one or more medical devices may be implanted to coordinate with LCP 502 to deliver rate responsive pacing therapy to heart 508. Regions 504A-B highlight regions in the upper pectoral regions of patient 500 near the clavicles. Region 506 illustrates another region where one or more medical devices may be implanted to coordinate with LCP 502 to deliver rate responsive pacing therapy to heart 508. Region 506 depicts an area in the chest region of patient 500 above the lung. In some examples, region 506 may include intercostal spaces between ribs of patient 500. One feature of both regions 504A-B and 506 is that each location may include at least a portion of a lung between the one or more medical devices and the LCP 502.

Accordingly, communication signals sent between a medical device in regions 504A-B and/or 506 and LCP 502 may pass through at least a portion of lungs 510, as indicated by communication lines 512.

Regions 504A-B and 506 are illustrative of only a few regions where one or more medical devices may be implanted to coordinate with LCP 502 to deliver rate responsive pacing therapy to heart 508. In other examples, medical device systems may include medical devices implanted in other regions of patient 500, sometimes where there is at least a portion of a lung between the implanted device or devices and LCP 502. As will be discussed later, when there is a portion of a lung between LCP 502 and another implanted device, the two devices may cooperate to determine a transthoracic impedance parameter over time, from which a respiration rate and/or tidal volume may be derived. The respiration rate and/or tidal volume may be indicative of a patient's activity level.

In order to deliver rate responsive pacing, a medical system may include a plurality of devices to help determine one or more parameters, as further described below. Although the examples described below only include one LCP and one other medical device, other medical device systems may have additional and/or different medical devices. In the examples described below, the medical device system includes an LCP, such as LCP 100, and another medical device, generally referred to as the other medical device (MD). The MD may represent any suitable medical device, including those described above with respect to FIGS. 1-3.

One example medical device system may include LCP 100 implanted within a patient's heart and another MD implanted within a patient's upper pectoral region such that a portion of the patient's lung is disposed between LCP 100 and the MD. The medical device system may be configured to determine a heart rate parameter. For example, LCP 100 may be configured to sense cardiac electrical activity. In some cases, LCP 100 may be configured to process the sensed cardiac electrical information using a peak detector and/or a QRS detector. For example, LCP 100 may count the number of peaks and/or QRS complexes that LCP 100 detects within a given period of time to determine a current heart rate. That is, if LCP 100 detects twenty-five peaks and/or QRS complexes within a fifteen second time period, LCP 100 may determine the heart rate to be one-hundred beats per minute (bpm). In some cases, LCP 100 may update the heart rate parameter every five, ten, or twenty-five second, or any other suitable time period as desired. In some instances, LCP 100 may update the heart rate parameter on a beat-by-beat basis. In some cases, and although not required, LCP 100 may communicate the heart rate parameter to the other MD. When so provided, the heart rate parameter may be communicated on a periodic basis, for example every one, five, ten, or twenty-five seconds, or any other appropriate time period.

In some examples, the other MD may include an accelerometer, for example as described with respect to FIGS. 1-3. In such examples, the MD may determine an activity level parameter based on signals from the accelerometer. In some cases, LCP 100 itself may not include an accelerometer, or may turn off any attached accelerometer, as LCP 100 may receive accelerometer data from the other MD. This may extend the battery life of LCP 100, as LCP 100 may not need to provide power to the connected accelerometer. The MD may additionally communicate the sensed/determined activity level parameter to LCP 100 via a patient activity data signal. In some cases, the MD may communicate the sensed/determined activity level parameter to LCP 100 on a periodic basis, such as every one, five, ten, or twenty-five seconds, or any other suitable time period as desired. In some examples, the MD may employ a duty cycle for determining a patient activity level. For example, the MD may measure the activity level of the patient for a period of ten seconds and then not measure the activity level of the patient for a period of five seconds, resulting in a duty cycle of two-thirds. In other examples, the duty cycle may be any other suitable value such as one-quarter, one-half, three-quarters. In such examples, the MD may conserve energy over the life of the device as compared to devices that continuously measure the patient activity level.

In some examples, LCP 100 and the other MD may coordinate to determine a transthoracic impedance parameter. In some cases, LCP 100 may determine the transthoracic impedance parameter, and in other examples, the other MD may determine the transthoracic impedance parameter. In some examples where LCP 100 determines the transthoracic impedance parameter, MD may deliver a voltage pulse to the patient. In some cases, MD may also measure an amplitude of the current generated during the delivered voltage pulse. MD may communicate the measured amplitude of the delivered current to the LCP 100. LCP 100, in turn, may measure the amplitude of the received voltage pulse. LCP 100 may generally measure a reduced voltage level relative to the voltage pulse applied by the MD, as there will be some voltage drop across the impedance of patient. Once LCP 100 has measured the amplitude of the received voltage pulse, and received the measured current amplitude from the MD, LCP 100 may determine a transthoracic impedance parameter using, for example, Ohm's Law. This is just one example, in another example, MD may determine a transthoracic impedance parameter using the measured amplitude of the received voltage pulse, without receiving a measured current amplitude from the MD.

When LCP 100 and the MD are separated by at least a portion of the patient's lung, the transthoracic impedance may change over time due to inhalation and exhalation of air from the patient's lungs. Accordingly, and in some cases, LCP 100 and the MD may cooperate to determine a transthoracic impedance parameter over time, and the medical device system may obtain information about the patient's respiration (e.g. breathing rate, tidal volume, etc.). In some examples, LCP 100 and the MD may coordinate to determine a transthoracic impedance parameter five times, three times, or one time a second. In other examples, LCP 100 and the MD may coordinate to determine a transthoracic impedance parameter once every two, five, or ten seconds, or any other suitable period of time.

In some examples, the MD may be configured to deliver a voltage pulse with a predetermined voltage amplitude. In such examples, MD may be programmed with the predetermined amplitude so that LCP 100 may be able determine a voltage drop from the MD to the LCP 100. For instance, the amplitude of the voltage pulse may be equal to the battery voltage of the battery connected to the MD. In other examples, MD may be configured to deliver a voltage pulse with a variable amplitude. In such examples, MD may be additionally configured to communicate the amplitude of the delivered voltage pulse to LCP 100. For example, the MD may be configured to periodically determine a lowest amplitude voltage pulse that LCP 100 may detect and deliver a voltage pulse at the determined amplitude level (or at a slightly increased amplitude level due to a safety margin) in order to conserve power of the MD. In still other examples, the voltage pulse may be part of the a patient activity data signal or some other signal communicated between the LCP 100 and the MD. By using existing communication pulses, the power required to determine the transthoracic impedance parameter may be reduced. However, even in such examples, the MD may still send a separate communication indicating a measured value of the current generated by the patient activity data signal, when desired.

In some instances, the MD may determine a transthoracic impedance parameter. In such examples, LCP 100 may generate a voltage pulse, measure an amplitude of a current generated by the delivered voltage pulse, and communicate the measured amplitude of the delivered current to the MD. The MD, in turn, may measure an amplitude of the received voltage pulse and, in combination with the received current amplitude, may determine a transthoracic impedance parameter. As in the above examples when LCP 100 determines the transthoracic impedance parameter, LCP 100 and the MD may cooperate to determine the transthoracic impedance parameter on a periodic basis. Additionally, in examples where the MD is not programmed with the amplitude of the delivered voltage pulse by LCP 100, LCP 100 may communicate such information to the MD.

In some examples, the voltage pulse used to determine a transthoracic impedance parameter may be a sub-threshold pulse, which is a voltage pulse that does not capture the heart. In some cases, the voltage pulse may be a communication pulse delivered by the telemetry module of LCP 100 or telemetry module 202 of the other MD. In still other examples, instead of sending a separate voltage pulse for determining the transthoracic impedance parameter, the voltage pulse may be a pacing pulse that is delivered by LCP 100 to stimulate contraction of the heart. Using the pacing pulse as the voltage pulse may save LCP 100 energy over the life of the device. However, in examples where LCP 100 is not periodically delivering pacing pulses, LCP 100 may be configured to send voltage pulses at least once every predetermined time period, such as once every one, three, five, or ten seconds, or any other suitable time period.

Based on the transthoracic impedance over time, the medical device system may determine other various parameters. For example, since the medical device system may know how the transthoracic impedance changes over time, the system may determine a tidal volume parameter and/or a respiration rate parameter. From the tidal volume parameter and the respiration rate parameter, the system may determine a minute ventilation parameter.

In some cases, LCP 100 may determine the transthoracic impedance parameter, as well as a tidal volume parameter, a respiration rate parameter, and/or a minute ventilation parameter.

In other cases, MD may determine the transthoracic impedance parameter, as well as a tidal volume parameter, a respiration rate parameter, and/or a minute ventilation parameter. In yet other example, LCP 100 and/or the MD may communicate one or more values necessary to determine a tidal volume parameter, a respiration rate parameter, and/or a minute ventilation parameter to the other device. Accordingly, in some examples, LCP 100 may determine the transthoracic impedance parameter, but the MD may determine a tidal volume parameter, a respiration rate parameter, and/or a minute ventilation parameter. In other instances, it may be the other way around.

More generally, LCP 100 and the MD may cooperate to identify an attenuation of an electrically conducted signal sent between the devices. For example, the MD may send a conducted signal to LCP 100. The MD may also communicate an amplitude of the conducted signal to LCP 100. LCP 100 may measure an amplitude of the received conducted signal, and determine an attenuation parameter. The attenuation parameter include information regarding the patient's respiration, which may be related to the patient's current activity level. For example, the LCP 100 may use the attenuation parameter to determine a measure related to tidal volume, respiration rate, and/or minute ventilation. Likewise, the LCP 100 may send a conducted signal to MD. The LDP 100 may also communicate an amplitude of the conducted signal to the MD. The MD may measure an amplitude of the received conducted signal, and determine an attenuation parameter. The MD may use the attenuation parameter to determine a measure related to tidal volume, respiration rate, and/or minute ventilation. In either case, LCP 100 and the MD may cooperate to determine such an attenuation parameter over time, such as on a periodic basis. As with the transthoracic impedance parameter, the attenuation parameter may change as a function of inhalation and exhalation of air from the patient's lung, which may be related to the patient's current activity level.

As the inhalation and exhalation of air from the lungs may cause attenuation of different types of signals, in some examples the delivered signal may not be an electrically conducted signal. For instance, in some examples, the signal may instead be a radiofrequency signal. In other examples, the signal may be an acoustic signal. Additionally, it is contemplated that the communication signals between LCP 100 and the MD may be any suitable type of signal, such as radiofrequency or acoustic signals. For instance, the patient activity data signal sent from the MD to the LCP 100 may be communicated by radiofrequency or acoustic signals. When so provided, LCP 100 and/or MD may be able to conserve energy by using the communicated patient activity data signal to determine an attenuation parameter and, in some cases, a tidal volume parameter, a respiration rate parameter, and/or a minute ventilation parameter.

As discussed above, LCP 100 and the MD may cooperate to determine a patient activity level, and to use the patient activity level to deliver rate responsive pacing therapy to the heart of the patient. In one example, LCP 100 may be configured to deliver pacing pulses to the heart of the patient and adjust the rate at which pacing pulses are delivered. LCP 100 may have a base pacing rate at which LCP 100 delivers pacing pulses. LCP 100 may compare the patient activity level to one or more thresholds to determine whether LCP 100 should deliver pacing pulses at a rate different than the base rate. Each region between thresholds may have an associated delivery rate. Accordingly, LCP 100 may determine that the patient activity level is above one of the thresholds but below another one of the thresholds. From this, LCP 100 may determine a delivery rate and adjusts the pacing rate of delivered pacing pulses to match the determined delivery rate. In other examples, LCP 100 may use the patient activity level as a value in a formula or lookup table to determine an appropriate pacing rate. In such examples, LCP 100 may periodically, or in some cases continuously, update the formula with the patient activity level to determine a pacing rate and adjust the pacing rate of delivered pacing pulses accordingly.

In some cases, LCP 100 may adjust the pacing rate of delivered pacing pulses based on a minute ventilation parameter, whether determined by LCP 100 or communicated to the LCP 100 from the MD. For example, LCP 100 may use one or more thresholds for determining a pacing rate, as described above with respect to the patient activity level. In other examples, LCP 100 may use a minute ventilation parameter as a value in a formula for determining a delivery rate. In such examples, LCP 100 may determine a delivery rate using the formula as described above with respect to the patient activity level, and may adjust the rate of delivered pacing pulses based on the determined delivery rate.

In still other examples, LCP 100 may use both the patient activity level and a minute ventilation parameter in determining a pacing rate. For instance, LCP 100 may compare the patient activity level to a first set of one or more thresholds to determine a first pacing rate. LCP 100 may additionally compare the minute ventilation parameter to a second set of one or more thresholds to determine a second pacing rate. LCP 100 may then determine a composite pacing rate, such as by averaging the pacing rates or by using another relationship or formula that may weight the determined first pacing rate and second pacing rate differently. LCP 100 may then adjust the pacing rate of delivered pacing pulses to the determined composite pacing rate. In some instances, LCP 100 may use both the patient activity level and a minute ventilation parameter as inputs into a pacing rate function. The pacing rate function may output a pacing rate using a formula or other relationship that includes a measure related to the patient activity level and a minute ventilation parameter as inputs. Other inputs may also be provided, if desired. LCP 100 may adjust the pacing rate of delivered pacing pulses to the determined pacing rate. These are just a few examples of how LCP 100 may determine a pacing rate for delivering pacing pulses to the heart in a rate responsive manner.

In some cases, LCP 100 may not determine a pacing rate. Rather, the MD may determine a pacing rate and communicate the determined pacing rate to the LCP 100. As described previously, the MD may in some cases have a larger battery than LCP 100, and thus having the MD determine the pacing rate may extend the battery life of the LCP 100. In such examples, the MD may determine a pacing rate using any of the methods described above with respect to LCP 100, or using in other suitable method. The MD may then communicate the determined pacing rate to the LCP 100, and the LCP 100 may adjust the pacing rate of delivered pacing pulses to the heart based on the received pacing rate.

In some examples, the MD may only communicate the delivery rate periodically instead of continuously. For example, LCP 100 may have a base pacing rate of delivery of pacing pulses. The MD may be programmed with this base pacing rate. Accordingly, the MD may only communicate a pacing rate to LCP 100 when MD determines a pacing rate that is different from the base pacing rate, sometimes by a predetermined amount. For example, the MD may only communicate a new pacing rate to the LCP 100 if the determined pacing rate differs from the base pacing rate by five or more beats per minute (bpm). In some instances, the MD may then repeatedly communicate an updated pacing rate to the LCP 100 until the determine pacing rate falls back down within the five beats per minute (bpm) threshold difference level. In some cases, the MD may only communicate an updated pacing rate to the LCP 100 when the new determined pacing rate differs from the current pacing rate by five or more beats per minute (bpm). For instance, the MD may determine a new pacing rate, and if the new pacing rate is five beats per minute (bpm) different than the current pacing rate of the LCP 100 (which may be the base pacing rate or some other pacing rate), then the MD may communicate the new pacing rate to the LCP 100. The MD may then communicate an updated pacing rate to the LCP 100 when the MD determines a new pacing rate that is different than the last communicated pacing rate by five beats per minute (bpm), such when the new pacing rate rises by five beats per minute (bpm) or falls by five beats per minute (bpm) relative to the previously communicated pacing rate. Of course, the use of five beats per minute (bpm) as a threshold is only exemplary, and in other examples, the MD may use thresholds of two, three, or ten beats per minute, or any other suitable threshold. In examples where LCP 100 has a base pacing rate of delivery, instead of communicating a new pacing rate, the MD may communicate a change in pacing rate from the base pacing rate. For example, if the base pacing rate is 60 bpm, and the determined pacing rate is 70 bpm, the MD may communicate a value of 10 bpm. The LCP may then add the communicate value (10 bpm) to the base pacing rate (60 bpm) to arrive at the determined pacing rate (70 bpm).

In still other examples, the MD may not send a pacing rate. Rather, the MD may control the pacing rate of LCP 100 by communicating a determined patient activity level, sometimes on a periodic or other basis. For example, the MD may communicate an activity level to LCP 100, such as when the patient activity level rises above or falls below one or more activity level thresholds. Once LCP 100 receives a patient activity level from the MD, LCP 100 may use the patient activity level to determine an appropriate pacing rate, and adjust the pacing rate of delivered pacing pulses to the newly determine pacing rate. In other examples, the MD may only send an updated patient activity level when the MD determines that the patient activity level changes by at least a first threshold amount. For example, the MD may only send an updated patient activity level when the patient activity level changes by more than five percent. However, the MD may use other thresholds such as two, three, seven, or ten percent, or any other appropriate percent. After the MD determines that the patient activity level changed by a threshold amount, the MD may then communicate the new patient activity level to LCP 100. After determining a change in the patient activity level by at least the first threshold amount, the MD may not send another communication of the patient activity level to LCP 100 until determining that the new patient activity level has changed by a second threshold amount. This second threshold amount may be the same or different than the first threshold amount. In this manner, the MD may control the pacing rate without sending a specific pacing rate to LCP 100.

In some examples, an accelerometer of an MD may be used, at least in part, to determine a patient activity level. Although not necessary, the accelerometer may be a three-axis accelerometer. When so provided, LCP 100 and the MD may cooperate to treat orthostatic hypotension. For example, the MD may monitor at least a vertical component of the three-axis accelerometer. More specifically, in some examples, the MD may compare a rate of change in the vertical component of the three-axis accelerometer to a threshold. If the rate of change is greater than a threshold, the MD may communicate a signal to LCP 100. In some examples, the signal may set a pacing rate that is higher than the current pacing rate. In other examples, the signal may itself communicate the rate of change in the vertical component of the three-axis accelerometer. In such examples, LCP 100 may determine an increased pacing rate based on the received signal from the MD. In these examples, the determined pacing rate may only last for a predetermined period of time. In other examples, the MD may send an additional communication with a reduced pacing rate or a reduced rate of change of the vertical component of the three-axis accelerometer to cause a reduced pacing rate.

In some instances, LCP 100 may incorporate additional parameters to the ones described above in delivering rate responsive pacing. For example, LCP 100 may have an active accelerometer. When so provided, LCP 100 may determine one or more heart sound parameters using the accelerometer. In some cases, LCP 100 may have additional sensors which allow LCP 100 to determine other parameters such as blood flow, blood pressure, oxygen content of the blood, temperature, and others. It is contemplated that such parameters may be used in determining an appropriate pacing rate for rate responsive pacing therapy.

Figure 6:
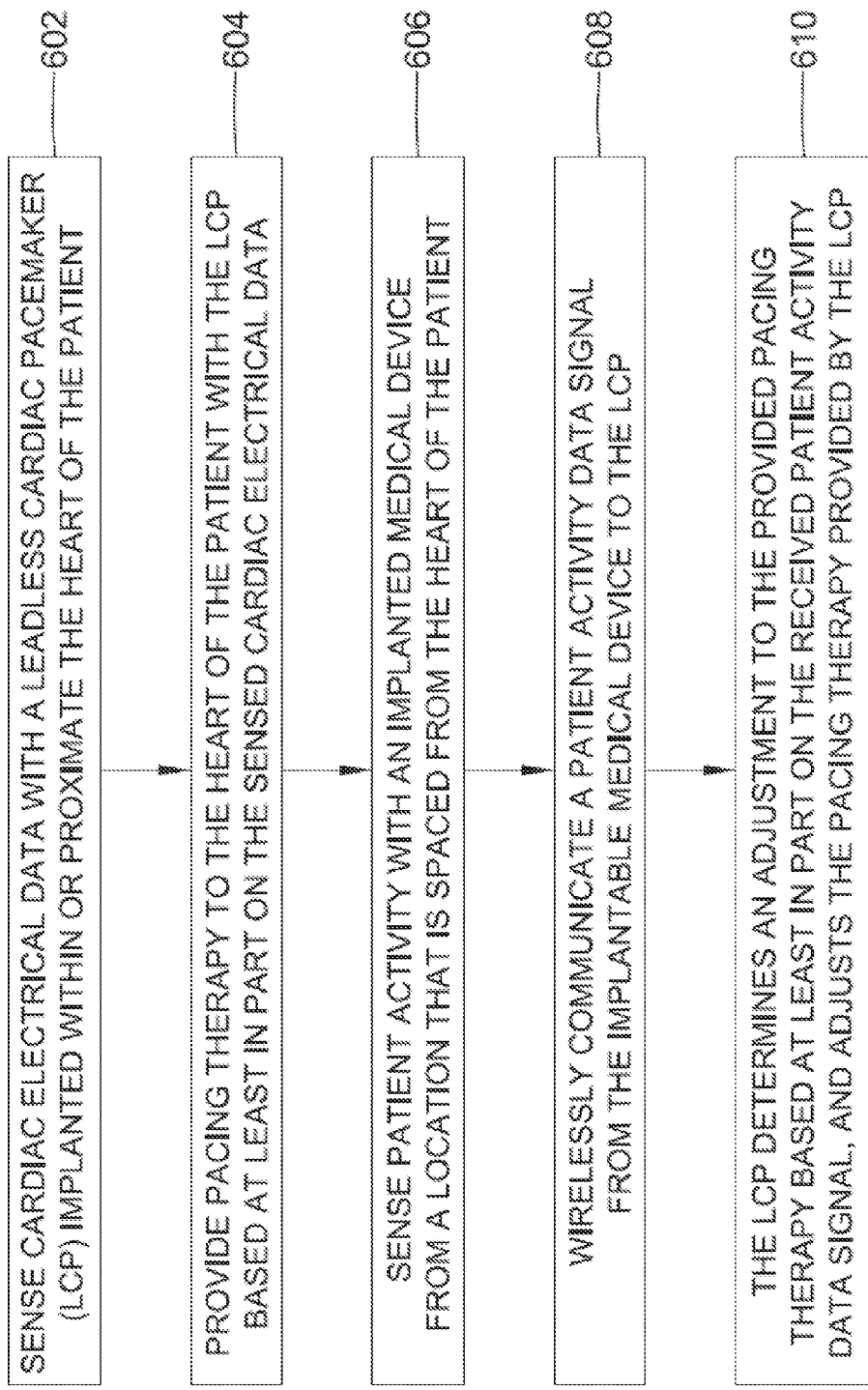
FIG. 6 is a flow diagram of an illustrative method that may be implemented by a medical device or medical device system, such as the illustrative medical devices and medical device systems described with respect to FIGS. 1-3.

FIG. 6 is a flow diagram of an illustrative method that may be implemented by an implantable medical device, such as one that includes LCP 100 and at least another medical device, for example any of the devices described with respect to FIGS. 1-3, whether including one or more leads or being leadless. Although the method of FIG. 6 will be described with respect to LCP 100 and an MD, the illustrative method of FIG. 6 may be performed by any suitable medical device or medical device system, as desired.

In some instances, a first implantable medical device, for instance LCP 100, may be implanted within or proximate a heart of a patient, and may sense cardiac electrical data, as shown at 602. LCP 100 may provide pacing therapy to the heart of the patient based at least in part on the sensed cardiac electrical data, as shown at 604. A second medical device (MD), for example any of the devices described with respect to FIGS. 1-3, may be implanted at a location that is spaced from the heart of the patient and may sense patient activity, as shown at 606. The MD may wirelessly communicate a patient activity data signal to the LCP 100, as shown at 608. LCP 100 may determine an adjustment to the provided pacing therapy based at least in part on the received patient activity data signal, and adjust the pacing therapy provided by the LCP 100, as shown at 610. In some cases, the LCP 100 may adjust the pacing rate based on the received patient activity data signal, to thereby provide rate responsive pacing by the LCP 100. In some cases, the patient activity data signal may represent a level of activity of the patient, such as derived from an accelerometer, respiration monitor or sensor and/or any other suitable sensor of the second medical device (MD). In some cases, the patient activity data signal may represent a desired pacing rate as determined by the MD.

Figure 7:
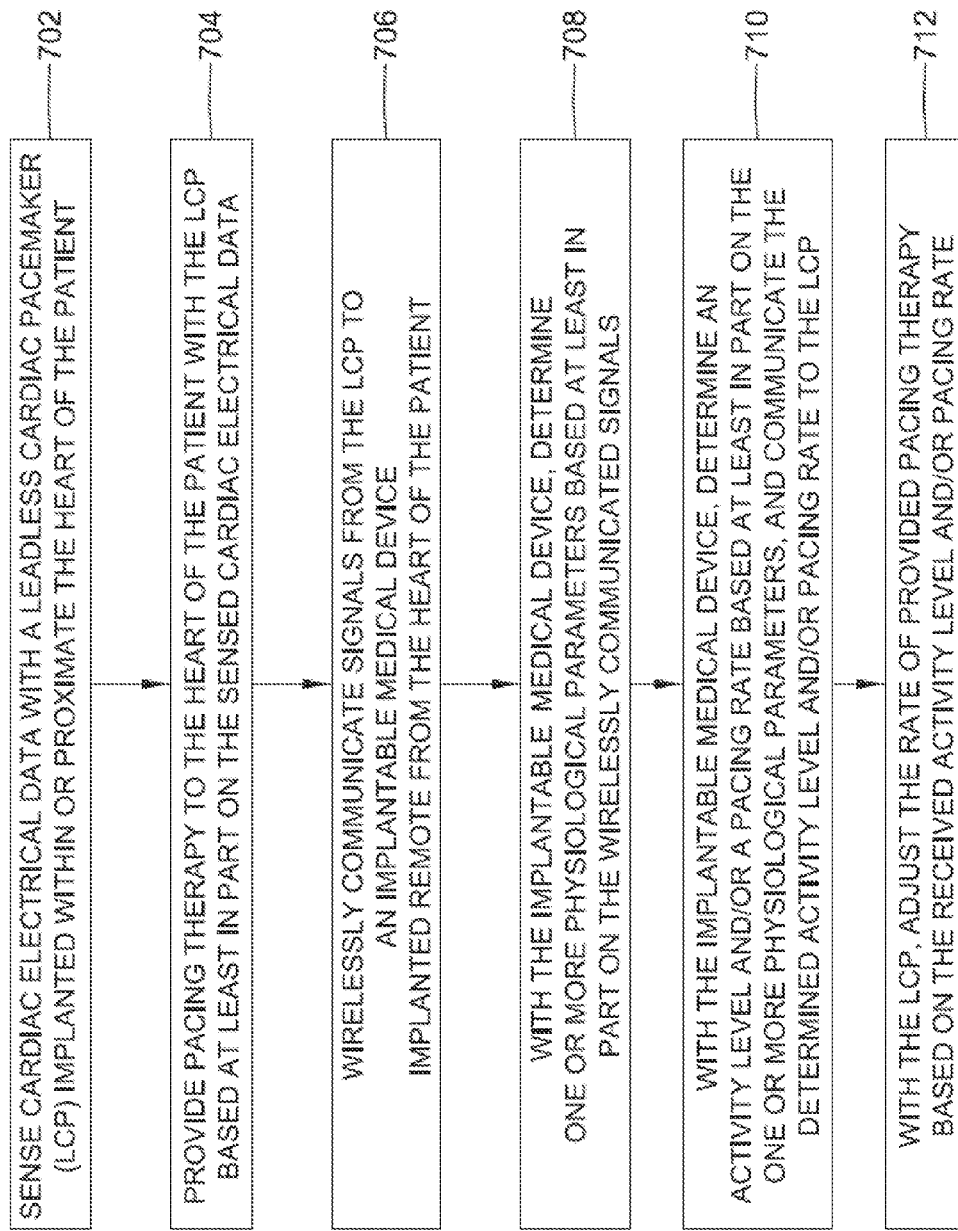
FIG. 7 is a flow diagram of another illustrative method that may be implemented by a medical device or medical device system, such as the illustrative medical devices and medical device systems described with respect to FIGS. 1-3.

FIG. 7 is a flow diagram of another illustrative method that may be implemented by an implantable medical device, such as one that includes LCP 100 and at least another medical device, for example any of the devices described with respect to FIGS. 1-3, whether including one or more leads or being leadless. Although the method of FIG. 7 will be described with respect to LCP 100 and MD, the illustrative method of FIG. 7 may be performed by any suitable medical device or medical device system.

In some examples, a first implantable medical device, for instance LCP 100, may be implanted within or proximate a heart of a patient and may be configured to sense cardiac electrical data, as shown at 702. LCP 100 may provide pacing therapy to the heart of the patient based at least in part on the sensed cardiac electrical data, as shown at 704. LCP 100 may wirelessly communicate signals to another medical device (MD), such as an implantable leadless medical device that is implanted remote from the heart of the patient, as shown at 706. The MD may determine one or more physiological parameters based at least in part on the wirelessly communicated signals, as shown at 708.

In some cases, the MD may determine an activity level and/or an updated pacing rate based, at least in part, on the one or more physiological parameters. The MD may then communicate the determined activity level and/or updated pacing rate to the LCP 100, as shown at 710. The LCP 100 may then adjust the pacing rate based on the received activity level and/or updated pacing rate, to thereby provide rate responsive pacing by the LCP 100, as shown at 712.

Figure 8:
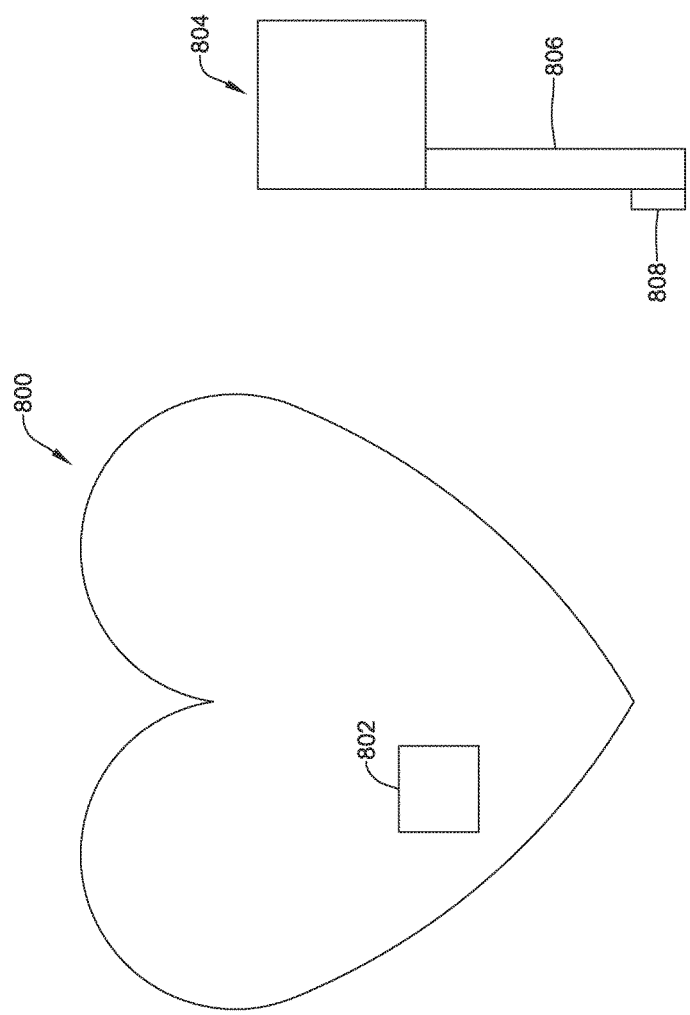
FIG. 8 is a schematic diagram of an exemplary medical system that includes a leadless cardiac pacemaker (LCP) implanted within the heart and an implantable cardioverter-defibrillator (ICD) exterior to the heart.

FIG. 8 shows a system 800 in which a leadless cardiac pacemaker (LCP) 802 is disposed within the heart. An implantable cardioverter-defibrillator (ICD) 804 is exterior to the heart. The ICD 804 includes a lead 806 and an electrode 808 disposed on the lead 806. The electrode 806 is implanted at a location that is spaced from the heart.

Those skilled in the art will recognize that the present disclosure may be manifested in a variety of forms other than the specific examples described and contemplated herein. For instance, as described herein, various examples include one or more modules described as performing various functions. However, other examples may include additional modules that split the described functions up over more modules than that described herein. Additionally, other examples may consolidate the described functions into fewer modules. Accordingly, departure in form and detail may be made without departing from the scope and spirit of the present disclosure as described in the appended claims.

What is claimed is:

1. An implantable medical device system for providing adjustable rate pacing therapy to a heart of a patient, the system comprising:
   a leadless cardiac pacemaker (LCP) configured to be implantable within or proximate the heart of the patient, wherein the LCP comprises a plurality of electrodes and a controller operably coupled to the plurality of electrodes, wherein the controller of the LCP is configured to:
   sense cardiac electrical data using two or more of the plurality of electrodes;
   provide pacing therapy to the heart of the patient using two or more of the plurality of electrodes, the pacing therapy based at least in part on the sensed cardiac electrical data;
   an implantable cardioverter-defibrillator (ICD) that has a lead with two or more electrodes that are implanted in a location that is spaced from the heart of the patient, wherein the ICD comprises a patient activity sensor and a controller operably coupled to the patient activity sensor, wherein the controller of the ICD is configured to:
   sense patient activity using the patient activity sensor, and
   wirelessly communicate a patient activity data signal to the LCP using the two or more electrodes; and
   wherein the controller of the LCP is configured to determine an adjustment to the provided pacing therapy based at least in part on the received patient activity data signal and to adjust the pacing therapy.

2. The system of claim 1, wherein the pacing therapy comprises a pacing rate, and wherein the adjustment to the provided pacing therapy comprises an adjustment to the pacing rate of the provided pacing therapy.

3. The system of claim 1, wherein the patient activity data signal is wirelessly communicated to the LCP by conducted communication.

4. The system of claim 1, wherein the patient activity sensor comprises an accelerometer.

5. The system of claim 4, wherein the controller of the LCP is further configured to determine the adjustment to the provided pacing therapy based at least in part on both the output of the accelerometer and a respiration rate of the patient that is determined at least in part using the ICD.

6. An implantable medical device system for providing adjustable rate pacing therapy to a heart of a patient, the system comprising:
a leadless cardiac pacemaker (LCP) configured to be implantable within or proximate the heart of the patient, the LCP including an LCP accelerometer, a plurality of electrodes and a controller operably coupled to the LCP accelerometer and the plurality of electrodes;
an implantable cardioverter-defibrillator (ICD) that has a lead with one or more electrodes that are implanted at a location that is spaced from the heart of the patient, wherein the ICD comprises an ICD accelerometer and a controller operably coupled to the one or more electrodes and the ICD accelerometer, and wherein the ICD is wirelessly communicatively coupled to the LCP;
wherein the controller of the ICD is configured to generate patient activity data based at least in part on an output of the ICD accelerometer, and is further configured to wirelessly communicate the patient activity data to the LCP; and
wherein the controller of the LCP is configured to:
provide rate responsive pacing therapy to the heart of the patient; and
adjust the rate of the rate responsive pacing therapy based at least in part on the patient activity data received from the ICD.

7. The implantable medical device system of claim 6, wherein the patient activity data is wirelessly communicated to the LCP by conducted communication using two or more electrodes of the LCP and two or more electrodes of the ICD.

8. The implantable medical device system of claim 6, wherein the patient activity data is wirelessly communicated to the LCP using one or more of an electrical signal, a radiofrequency signal and an acoustic signal.

9. A method for providing rate responsive pacing therapy to a heart of a patient, the method comprising:
sensing cardiac electrical data with a leadless cardiac pacemaker (LCP) implanted within the heart of the patient;
providing pacing therapy to the heart of the patient with the LCP based at least in part on the sensed cardiac electrical data;
sensing patient activity with an implantable cardioverter-defibrillator (ICD) that has a lead with an electrode, wherein the electrode of the lead is implanted at a location that is spaced from the heart of the patient, and the ICD determining a patient activity data signal based upon the patient activity sensed by the ICD;
wirelessly communicating the patient activity data signal from the ICD to the LCP;
the LCP adjusting the pacing therapy provided by the LCP based at least in part on the received patient activity data signal; and
wherein the pacing therapy comprises a pacing rate, and the adjustment to the provided pacing therapy includes an adjustment to the pacing rate.

10. The method of claim 9, wherein the patient activity data signal is wirelessly communicated to the LCP by conducted communication.

11. The method of claim 9, wherein the patient activity data signal comprises one or more of an electrical signal, a radiofrequency signal and an acoustic signal.

12. The method of claim 9, wherein the patient activity data signal is based, at least in part, on an output of an accelerometer of the ICD.

13. The method of claim 12, wherein the LCP adjusts the provided pacing therapy based at least in part on both the output of the accelerometer of the ICD and a respiration rate of the patient that is determined at least in part using the ICD.

14. The method of claim 9, wherein the patient activity data signal comprises accelerometer data.

15. The method of claim 9, wherein the patient activity data signal is based, at least in part, on a respiration signal.

16. The method of claim 15, wherein the respiration signal is based, at least in part, on a measure related to an impedance across at least a portion of a lung of the patient.

17. The method of claim 15, wherein the respiration signal is based, at least in part, on an amplitude of the patient activity data signal received at the LCP, and wherein the LCP adjusts the provided pacing therapy based at least in part on the respiration signal.

18. The method of claim 9, wherein the LCP adjusts the provided pacing therapy based at least in part on a sensed heart rate of the patient.

19. The method of claim 18, wherein sensed heart rate of the patient is sensed by one or more exposed electrodes of the LCP.

* * * * *